United States Patent [19]

Soudant et al.

[11] Patent Number: 5,712,311

[45] Date of Patent: Jan. 27, 1998

[54] COSMETIC OR DERMATOLOGICAL COMPOSITION WITH CONTROLLED RELEASE OF ACTIVE PRINCIPLE CONTAINING A PHOTOCONVERTIBLE CAROTENOID

[75] Inventors: Etienne Soudant, Fresnes; Constantin Koulbanis, Le Kremlin Bicetre, both of France

[73] Assignee: L'Oreal, Paris, France

[21] Appl. No.: 662,257

[22] Filed: Jun. 14, 1996

[30] Foreign Application Priority Data

Jun. 16, 1995 [FR] France .................. 95 07211

[51] Int. Cl.⁶ .................. A61K 31/19; A61K 31/215; A61K 31/045; A61K 31/015
[52] U.S. Cl. .................. 514/572; 424/59; 424/60; 424/400; 424/401; 514/529; 514/729; 514/762; 514/763
[58] Field of Search .................. 424/59, 60, 400, 424/401; 514/529, 572, 729, 762, 763

[56] References Cited

U.S. PATENT DOCUMENTS

| 3,920,834 | 11/1975 | Klaui et al. .................. 424/305 |
| 4,603,146 | 7/1986 | Kligman .................. 514/559 |
| 4,877,805 | 10/1989 | Kligman .................. 514/381 |
| 4,888,342 | 12/1989 | Kligman .................. 514/419 |
| 5,438,073 | 8/1995 | Saurat et al. .................. 514/452 |

FOREIGN PATENT DOCUMENTS

| 0 467 795 | 1/1992 | European Pat. Off. . |
| 0 631 772 | 1/1995 | European Pat. Off. . |

OTHER PUBLICATIONS

Advertisement for "DayWear", Vogue Magazine, Aug. 1995.
Packaging and package insert for "DayWear" product, Estee Lauder, New York.

Mordi, Raphael C., "Carotenoids: Functions and Degradation", Chemistry & Industry, 1 Feb. 1993, pp. 79–83.

*Primary Examiner*—Shelley A. Dodson
*Attorney, Agent, or Firm*—Jacobson, Price, Holman & Stern, PLLC

[57] ABSTRACT

The invention relates to a cosmetic or dermatological composition with controlled release of active principle containing at least photoconvertible carotenoid, capable of being converted to retinol and retinoic acid or its isomers, of following formula (I):

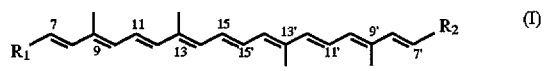

in which the $R_1$ and $R_2$ substituents denote one of the following groups:

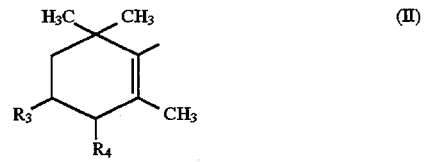

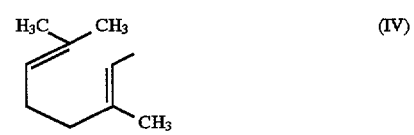

at least one of the $R_1$ and $R_2$ substituents denoting a β-ionone group of formula (II), the $R_3$ and $R_4$ substituents denoting hydrogen, a hydroxyl, carboxyl or $C_1$–$C_4$ alkoxy group or forming, with the carbon atom of the ring, a carbonyl group, in a cosmetically or dermatologically acceptable medium.

16 Claims, No Drawings

COSMETIC OR DERMATOLOGICAL COMPOSITION WITH CONTROLLED RELEASE OF ACTIVE PRINCIPLE CONTAINING A PHOTOCONVERTIBLE CAROTENOID

The present invention relates to the use of a photoconvertible carotenoid for protecting the skin against photoaging and for preventing acne and to a cosmetic or dermatological composition with controlled release of active principle containing a photoconvertible carotenoid.

Retinoic acid has already been used under the name of "vitamin A acid", for example in Application EP 230 498, in compositions intended for controlling photoaging of the skin.

The retinoids used in dermatology are generally retinoic acid and its isomers and have a true biological activity. However, they have serious side effects, whether used systemically or topically, and in particular are highly irritating to the skin.

This is why, according to French Patent Application 2 681 784, use is made in dermatology, stomatology or cosmetology, in particular for the treatment of complaints such as psoriasis, acne, eczema, and the like, for the treatment of ailments of the mucous membranes or for the treatment of disorders due to aging and/or of seborrhoea, of bioprecursors of retinoic acid or retinol which, when they are brought into contact with epidermal cells, bring about the biosynthesis of retinoic acid and/or of retinol via enzymatic systems specific to each cell. Mention may be made, among these bioprecursors, in particular of retinal, which results in the intracellular formation of retinol and of retinoic acid.

The Applicant Company has discovered surprisingly that the retinoids which are useful in cosmetology and dermatology, such as retinol and retinoic acid and its isomers, could be released on the skin in a controlled way by photoconversion of carotenoids via hydrophilic activated forms of oxygen.

Such a photoconversion can take place under the effect of an "oxidative stress", that is to say any external atmospheric attack which generates hydrophilic activated forms of oxygen. Such an "oxidative stress" can be the result of UV irradiation or alternatively of pollution.

The subject of the present invention is therefore the use of a photoconvertible carotenoid of formula:

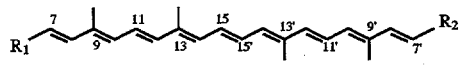
(I)

in which the $R_1$ and $R_2$ substituents denote one of the following groups:

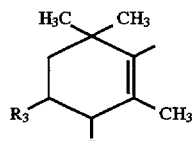
(II)

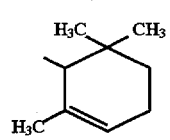
(III)

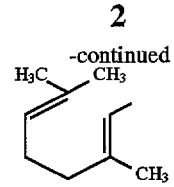
(IV)

at least one of the $R_1$ and $R_2$ substituents denoting a β-ionone group of formula (II), the $R_3$ and $R_4$ substituents denoting hydrogen, a hydroxyl, carboxyl or $C_1$–$C_4$ alkoxy group or forming, with the carbon atom of the ring, a carbonyl group, for the treatment of the skin for the purpose of protesting it or of controlling photoaging and for the prevention of acne or the control of acne.

The $C_1$–$C_4$ alkoxy group is preferably a methoxy group.

The carotenoid of formula (I) is more particularly chosen from β-carotene, α-carotene, γ-carotene, canthaxanthin, lutein, zeaxanthin and astaxanthin.

The photoconvertible carotenoids of formula (I) used according to the invention are precursors of retinoids which, under the effect of an "oxidative stress", release retinol and retinoic acids in a controlled way. This release is, as it were, programmed by the stress and, for this reason, the composition only acts when the need for it makes itself felt.

Another subject of the invention is a cosmetic or dermatological composition with controlled release of active principle containing at least one carotenoid capable of being converted to retinol and retinoic acid and its isomers having the formula (I) above.

The cosmetic or dermatological composition with controlled release of active principle according to the invention is intended in particular for the prevention of photoaging and of acne and/or for the control of acne and of photoaging.

In its application to the prevention of photoaging and/or to the control of photoaging, the cosmetic or dermatological composition according to the invention provides a feeling of comfort and of softness, makes it possible to tone down red blotches on the face, as well as wrinkles and fine lines, by reducing the roughness of the skin, and gives radiance and uniformity to the complexion, while being well tolerated.

The cosmetic or dermatological composition according to the invention contains 0.0001 to 10% by weight, and preferably 0.0001 to 5% by weight, of at least one carotenoid of formula (I) as defined above, in a cosmetically or dermatologically acceptable medium.

The cosmetic or dermatological composition according to the invention can additionally contain at least one cosmetic or dermatological active principle chosen from anti-inflammatories, anti-acne agents, anti-fungals, antibacterials, antiseborrhoeic agents, vitamins, keratolytic agents, humectants, agents for combating free radicals and antioxidants.

Another subject of the present invention is the use of a photoconvertible carotenoid of formula (I) as defined above for the manufacture of a cosmetic or dermatological composition intended for the prevention of photoaging or for the control of photoaging of the skin or intended for the prevention of acne or for the control of acne.

The cosmetic or dermatological compositions according to the invention can be formulated, for example, in the form of an emulsion, in particular of a cream, in the form of a gel, of a powder, of anhydrous product, of an oil-in-water emulsion formed by oily globules provided with a lamellar liquid crystal coating, as described in EP-A-0 641 557, or alternatively of an aqueous dispersion of vesicles containing liposomes, niosomes or nanocapsules. A liposome is a vesicle in which the membrane is composed of ionic lipids and a "niosome" is a vesicle in which the membrane is composed of non-ionic lipids. The vesicular systems are obtained according to conventional techniques, for example according to Patent Applications FR-A-2 315 991, 2 408 387, 2 597 346 and 2 597 367. The nanocapsules are prepared from emulsified polymers, in particular according to Patent Application FR-A-2 659 554.

Another subject of the invention is a process for the cosmetic treatment of the skin which comprises the application, before exposure to ultraviolet radiation, of a sufficient mount of a cosmetic composition as defined above.

The invention will be better illustrated using the following non-limiting examples.

EXAMPLE 1: DAY CREAM BASED ON LIPOSOMES

In a first stage, a liposomed aqueous dispersion is prepared which comprises:

Phytosterol oxyethylenated with 5 mol of ethylene oxide 1.2 g

Hydrogenated soya lecithin 1.8 g

β-Carotene 0.3 g

Glycerol 3 g

Demineralized water 15 g

In a second stage, the following fatty phase is added to the liposomed phase:

Apricot oil 10 g

Cyclodimethicone 5 g

The whole mixture is subjected to mechanical stirring and then the following substances are added:

Carboxyvinyl polymer (mixture of carboxyvinyl acids marketed under the name of Carbopol 940 by the Company Goodrich) 0.4 g Preservative 0.3 g Triethanulzmine q.s. pH=6

Demineralized water q.s 100 g

The β-carotene is thus stabilized in the membrane of the lipid vesicles.

Applied to the face every morning for a period of 1 to 3 months, this cream makes it possible to tone down wrinkles and fine lines, confers a smooth appearance on the skin and gives a radiant and uniform complexion.

EXAMPLE 2: DAY CREAM BASED ON "NIOSOMES" (NON-IONIC LIPIDS)

The following lipids are melted together, under an inert atmosphere, at 110° C.:

Dicetyl phosphate 0.3 g

Polyglycerol hexadecyl ether 1.35 g

Cholesterol 1.35 g

The temperature of the molten mixture is brought back to 90° C.

0.3 g of β-carotene is added.

A lamellar phase is then formed by adding the following aqueous phase:

Glycerol 3 g

Demineralized water 15 g

The mixture is homogenized at a temperature of 60° C.

The following fatty phase is then added at room temperature:

Liquid petrolatum 10 g

Isohexadecane 3 g

Cyclohexadimethicone 2 g

Introduction is carried out into an ultradisperser.

The following gelled phase is added:

Carboxyvinyl polymer (mixture of carboxyvinyl acids marketed under the name of Carbopol 940 by the Company Goodrich) 0.4 g Preservative 0.3 g Triethanolamine q.s. pH=6

Demineralized water q.s 100 g

EXAMPLE 3: POWDER

An emulsion is prepared at 60° C. from the following constituents:

Sodium caseinate 60 g

Xanthan gum 30 g

Apricot oil 198 g

Vitamin E 5 g

β-Carotene 2 g

Water 705 g

The emulsion is dehydrated by spraying.

A powder is obtained which can be applied directly to the skin of the face in the morning.

This powder confers a smooth appearance on the skin, correcting wrinkles and fine lines, makes it possible to thicken it and confers a more radiant complexion.

EXAMPLE 4: ANHYDROUS PRODUCT

The following composition is prepared:

Liquid petrolatum 14.5 g

Microcrystalline wax 30 g

Polyethylene filler 15 g

Apricot oil 5 g

Karite butter 20 g

β-Carotene 0.5 g

Carnauba wax 15 g

The stability of the β-carotene is conferred by the anhydrous medium.

This product, applied to the skin of the face every morning for 1 to 3 months, tones down wrinkles and fine lines, conferring a smooth appearance on it, and gives a more radiant complexion.

We claim:

1. A process for the cosmetic treatment of the skin for the purpose of protecting it against photoaging which comprises applying to the skin an effective amount for protecting it of a photoconvertible carotenoid capable of being converted to retinol and retinoic acid or its isomers of formula:

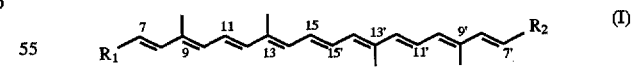

(I)

in which the $R_1$ and $R_2$ substituents denote one of the following groups:

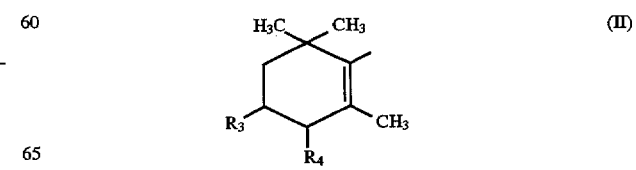

(II)

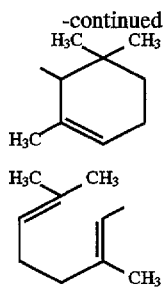

at least one of the $R_1$ and $R_2$ substituents denoting a β-ionone group of formula (II), the $R_3$ and $R_4$ substituents being selected from the group consisting of hydrogen, hydroxyl, carboxyl and $C_1$–$C_4$ alkoxy or forming, with the carbon atom of the ring, a carbonyl group.

2. The process of claim 1 wherein the $C_1$–$C_4$ alkoxy group is methoxy.

3. The process of claim 1 wherein the photoconvertible carotenoid of formula (I) is selected from the group consisting of β-carotene, α-carotene, γ-carotene, canthaxanthin, lutein, zeaxanthin and astaxanthin.

4. A cosmetic or dermatological composition with controlled release of active principle, which contains at least one photoconvertible carotenoid, capable of being converted to retinol and retinoic acid or its isomers, of following formula (I):

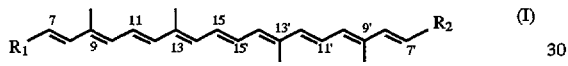

in which the $R_1$ and $R_2$ substituents denote one of the following groups:

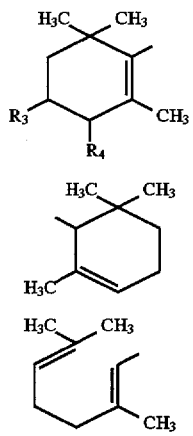

at least one of the $R_1$ and $R_2$ substituents denoting a β-ionone group of the formula (II), the $R_3$ and $R_4$ substituents being selected from the group consisting of hydrogen, hydroxyl, carboxyl and $C_1$–$C_4$ alkoxy or forming, with the carbon atom of the ring, a carbonyl group. in a cosmetically or dermatologically acceptable medium.

5. The composition of claim 4, wherein the $C_1$–$C_4$ alkoxy group is methoxy.

6. The composition of claim 4, which contains 0.0001 to 10% by weight of at least one compound of formula (I), in a cosmetically or dermatologically acceptable medium.

7. The composition of claim 6, which contains 0.0001 to 5% by weight of at least one compound of formula (I).

8. The composition of claim 4, which comprises at least one compound of formula (I) selected from the group consisting of β-carotene, α-carotene, γ-carotene, cantaxanthin, lutein, zeaxanthin and astaxanthin.

9. Cosmetic or dermatological composition according to claim 4, which additionally contains at least one cosmetic or dermatological active principle selected from the group consisting of anti-inflammatories, anti-acne, agents, antifungals, anti-bacterials, antiseborrhoeic agents, vitamins, keratolytic agents, humectants, agents for combating free radicals and antioxidants.

10. Cosmetic or dermatological composition according to claim 4, which is in the form of an emulsion, of a gel, of an aqueous dispersion of vesicles, of a powder or of an anhydrous product.

11. A process for the cosmetic treatment of the skin, which comprises the application to the skin, before exposure to ultraviolet radiation, of a sufficient amount of a cosmetic composition according to claim 4 for preventing or controlling photoaging of the skin.

12. A process for toning down wrinkles and fine lines on the skin, which comprises applying to the skin of tire face an effective amount of a cosmetic composition according to claim 4 every morning for 1 to 3 months.

13. A process for the prevention or control of acne which comprises applying to the skin an effective amount of a dermatological composition according to claim 4.

14. A process for the prevention or control of acne which comprises applying to the skin an effective amount of a carotenoid of formula:

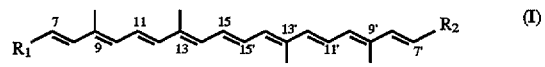

in which the $R_1$ and $R_2$ substituents denote one of the following groups:

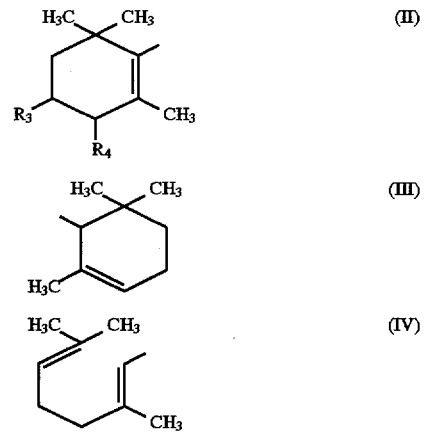

at least one of the $R_1$ end $R_2$ substituents denoting a β-ionone group of formula (II), the $R_3$ and $R_4$ substituents being selected from the group consisting of hydrogen, hydroxyl, carboxyl and $C_1$–$C_4$ alkoxy or forming, with the carbon atom of the ring, a carbonyl group.

15. The process of claim 14, wherein the $C_1$–$C_4$ alkoxy group is methoxy.

16. The process of claim 14, wherein the carotenoid is selected from the group consisting of β-carotene, α-carotene, γ-carotene, canthaxanthin, lutein, zeaxanthin and astaxanthin.

* * * * *